(12) United States Patent
Ciolkosz et al.

(10) Patent No.: US 7,955,059 B2
(45) Date of Patent: Jun. 7, 2011

(54) FLUID CONTROL DEVICE FOR A HIGH PRESSURE ANALYTICAL INSTRUMENT

(75) Inventors: Theodore D. Ciolkosz, Milton, MA (US); Peter Kirby, Derry, NH (US); Mark W. Moeller, Kingston, MA (US); Russell Keene, Sudbury, MA (US); Daniel J. McCormick, Westford, MA (US); Charles Murphy, Uxbridge, MA (US); Joseph A. Luongo, Walpole, MA (US); David R. Friswell, Upton, MA (US); Theodore Dourdeville, Marion, MA (US)

(73) Assignee: Waters Technologies Corporation, Milford, MA (US)

( * ) Notice: Subject to any disclaimer, the term of this patent is extended or adjusted under 35 U.S.C. 154(b) by 912 days.

(21) Appl. No.: 10/598,031

(22) PCT Filed: Mar. 2, 2005

(86) PCT No.: PCT/US2005/006672
§ 371 (c)(1),
(2), (4) Date: May 21, 2007

(87) PCT Pub. No.: WO2005/093256
PCT Pub. Date: Oct. 6, 2005

(65) Prior Publication Data
US 2008/0020136 A1    Jan. 24, 2008

Related U.S. Application Data

(60) Provisional application No. 60/550,972, filed on Mar. 5, 2004, provisional application No. 60/577,405, filed on Jun. 4, 2004.

(51) Int. Cl.
*F04B 39/04* (2006.01)
*F16K 15/04* (2006.01)
(52) U.S. Cl. ............... 417/454; 137/533.11; 137/533.13; 137/533.15
(58) Field of Classification Search .................. 417/454; 137/375, 533.11–533.15
See application file for complete search history.

(56) References Cited

U.S. PATENT DOCUMENTS
4,139,469 A    2/1979    Rainin et al.
(Continued)

OTHER PUBLICATIONS

English translation of Notice of Rejection for Japanese Patent Application No. 2007-501914 mailed Jun. 8, 2010 (4 pages).

*Primary Examiner* — Charles G Freay
(74) *Attorney, Agent, or Firm* — Anthony J. Janiuk; William G. Guerin

(57) ABSTRACT

In various embodiments a fluid control device suitable for high pressure analytical instruments includes a housing having an interior surface with an end wall. The interior surface defines a chamber. A valve assembly disposed in the chamber controls the flow of fluid through the chamber. An end cap is disposed in the housing opposite the end wall to enclose the chamber. The end wall and end cap each have an opening to pass a fluid to the chamber or to remove a fluid from the chamber. The housing and end cap each has an abutment surface to receive the other abutment surface. At least one of the abutment surfaces has a plastic seal coating. A means of compression, such as a compression housing and compression sleeve, is included to engage the end cap to deform the plastic seal coating between the abutment surfaces and thereby seal the chamber.

11 Claims, 4 Drawing Sheets

U.S. PATENT DOCUMENTS

| | | | |
|---|---|---|---|
| 4,387,736 A * | 6/1983 | Major | 137/550 |
| 4,945,945 A * | 8/1990 | Schmid | 137/512 |
| 4,974,628 A | 12/1990 | Tepermeister | |
| 5,605,449 A * | 2/1997 | Reed | 417/454 |
| 7,255,328 B2 * | 8/2007 | Hunter | 251/326 |
| 2005/0115840 A1 * | 6/2005 | Dolan | 205/324 |

* cited by examiner

FLUID CONTROL DEVICE FOR A HIGH PRESSURE ANALYTICAL INSTRUMENT

CROSS REFERENCE TO RELATED APPLICATIONS

This application claims priority from U.S. Provisional Patent Application No. 60/550,972, filed Mar. 5, 2004 and Application Ser. No. 60/577,405, filed Jun. 4, 2004. The contents of these applications are incorporated herein by reference.

STATEMENT ON FEDERALLY SPONSORED RESEARCH

N/A

Embodiments of the present invention are directed to devices and method for coupling, or joining components for receiving and discharging fluids. Devices made in accordance with the present invention have special application to fittings, valves and check valves.

BACKGROUND OF THE INVENTION

The present invention is directed to devices for receiving and discharging fluids. Devices embodying features of the present invention include, by way of example, without limitation, tees, unions, fittings, valves and check valves. These devices are sometimes placed in line between two or more conduits that are joined in the form of a union, or tee, or valve. The term "union" is used in the sense of joining or bringing together. A "tee" is a form of fitting in which fluid flow is split or combined. The devices are sometimes part of a larger structure in which the device communicates through ports or openings. This application will use the term "fluid path means" to mean all conduits, tubing, pipes, openings or ports which convey or transport fluids.

In this application, the term fitting will be used in the broadest sense to refer to a device that may be placed in a larger structure, for example, a pump assembly, or in line.

The term "valve" is used in a conventional manner to denote a device that can stop fluid flow in a conduit or pipe. A check valve is a special valve that allows fluid to flow in one direction only.

Fitting and valves of the prior art typically have gaskets and seals that are separate and discrete parts. These gaskets and seals exhibit material creep, cold flow and relaxation. That is, as the fluid pressure fluctuates, the gaskets move. This movement can lead to the gasket slipping from an original position, leading to gasket or seal failure.

This movement also creates a rebound of the gasket as the pressure is released, creating a potential pressure ripple. Analytical instruments, in particular, are sensitive to the rebound and pressure ripple effect.

These problems are amplified as the pressure contained by such devices increases. Analytical instruments, such as chromatography pumps and detectors typically operate at pressures of up to 3,000 to 4,000 pounds per square inch (psi). It is desirable to have analytical instruments operate at higher pressures, however, fittings, valves and check valves have a high failure rate at pressures greater than 3,000 psi.

SUMMARY OF THE INVENTION

Embodiments of the present invention feature devices and methods for holding fluids at high pressures. One embodiment of the present invention features a device for receiving and discharging fluids. The device comprises a first housing having at least one side wall. The side wall has an interior surface defining at least one chamber and has at least one end cap abutment surface for receiving an end cap. The device has at least one end cap having at least one first housing abutment surface. The first housing abutment surface receives the end cap abutment surface positioning the end cap on the first housing for enclosing the chamber. At least one of the first housing abutment surface and the end cap abutment surface has first seal coating. The first seal coating comprises a deformable plastic adhering to the abutment surface. The device further comprises a fluid path means for receiving and removing fluid from the chamber. And, the device comprises compression means to compress the end cap, with the end cap abutment surface received on said first housing abutment surface, towards said first housing to deform said first seal coating and seal said chamber.

Preferably, the seal coating is selected from one or more of the polymeric coatings consisting of polytrifluoroethylene (PTFE), polyetheretherketone (PEEK), polychlorotrifluoroethylene (PCTFE), perfluoroalkoxy (PFA) and fluorinated-ethylenepropylene (FEP).

As used herein, the term "fluid path means" refers to openings, ports, conduits and pipes that provide fluid. Thus, embodiments of the present invention can be placed in line, with fluid path means comprising conduits and pipes or incorporated within the housing of a larger structure, for example, without limitation, a pump head or pump housing.

Preferably, the end cap abutment surface and/or the housing abutment surface is a ridge to localize compression forces on said seal coating. The ridge is a relatively narrow protrusion capable of contact with an opposing abutment surface.

Embodiments of the present invention are ideally suited for fittings and valves. Where the device is in the form of a valve, the chamber contains a valve assembly. The valve assembly may comprise rotary-type valves, gated valves or check valves.

In the case where the device is in the form of a check valve, the first housing has at least one end wall opposite the end cap. The fluid path means comprises at least one opening in said end cap and at least one opening in said end wall. And, the chamber holds a valve assembly comprises a ball seat and a ball.

Preferably, the interior wall and/or the end cap has a ball seat abutment surface. And, the ball seat comprises a cylinder having a two rims, and a fluid passage. At least one of the rims has a ball receiving surface for engaging the ball and closing the fluid passage. And, at least one of the rims has a rim abutment surface for engaging the ball seat abutment surface and sealing the ball seat and the housing and/or end cap.

Preferably, the ball seat abutment surface and/or rim abutment surface has a ball seat seal coating. Preferably, the ball seat coating is made and formed as described above with respect to the seal coating.

Preferably the first housing end wall has an interior surface and an exterior surface, and one or more end wall openings. And, the exterior surface has an end wall abutment surface encircling the one or more end wall openings. Preferably, the end wall abutment surface has an end wall seal coating, the end wall seal coating comprising a deformable plastic to sealably engage an adjoining wall. Preferably, the end wall seal coating is made and formed as described above with respect to the seal coating. Devices of this type are well suited to be mounted in a further major housing structure having the adjoining wall. For example, without limitation, the end wall seal coating would engage the adjoining wall of a pump head housing. In this embodiment, preferably, the adjoining wall has an adjoining wall opening for the passage of fluid into the end wall opening. In this embodiment, the compression means comprises such adjoining wall for receiving the end wall and compressing the end wall seal coating in sealing engagement.

For inline application, preferably, the compression means comprises a compression housing assembly comprising a compression housing and compression sleeve. The compression housing has a compression chamber for receiving the housing. The compression sleeve engages the end cap for placing the end cap, and first housing under compression.

Preferably, the compression housing assembly has a compression nut. The compression nut and compression housing have cooperating threads which engage upon relative rotation of the compression nut and compression housing. The compression nut engage the compression sleeve to compress the compression sleeve, end cap and first housing within the compression housing chamber.

A further embodiment of the present invention comprises a method of joining fluid passages. One embodiment of the present method comprises the steps of providing a device having a first housing having a at least one side wall. The side wall has an interior surface defining at least one chamber, and has at least one end cap abutment surface for receiving an end cap. The device has at least one end cap. The end cap has at least one first housing abutment surface and is capable of being received on the first housing abutment surface for enclosing said chamber. The device has a first seal coating on at least one of the first housing abutment surface and the end cap abutment surface. The first seal coating comprises a deformable plastic adhering to the abutment surface. The device has a fluid path means for receiving and removing fluid from the chamber; and compression means to compress the end cap, with said end cap abutment surface received on said first housing abutment surface, towards said first housing to deform said first seal coating and seal said chamber. The method further comprises the step of placing the receiving conduit and discharge conduits in communication with the fluid passages.

Embodiments of the present method can be practiced with any of the devices of the present invention described above. The devices and methods of the present invention are ideally suited for high pressure applications. These high pressure applications include pressures of 4000 psi and greater.

The devices made in accordance of the present invention do not have seals that exhibit material creep, cold flow and relaxation. That is, as the fluid pressure fluctuates, the seal coating do not move. The seal coatings are adhered to or fixed to one of the abutment surfaces. As such the seal coating can not move or slip from an original position. Thus, embodiments of the present invention provide devices that do not have gasket failure.

Nor do devices of the present invention exhibit rebound pressure ripple due to gasket movement as the pressure is released. Analytical instruments, in particular, having devices made in accordance with the present invention are less sensitive to pressure fluctuations. These features and advantages will be apparent to those skilled in the art to which this invention relates upon viewing the Figures and reading the detailed description that follows.

DETAILED DESCRIPTION OF THE INVENTION

Embodiments of the present invention will now be described with respect to the Figures, with the understanding that the Figures and description are directed to the preferred embodiments of the present invention. For example, the present invention will be described in detail with respect to a check valve. Individuals skilled in the art will recognize that features of the present invention have application in many devices which hold or transport fluids under pressure.

Figure 1:
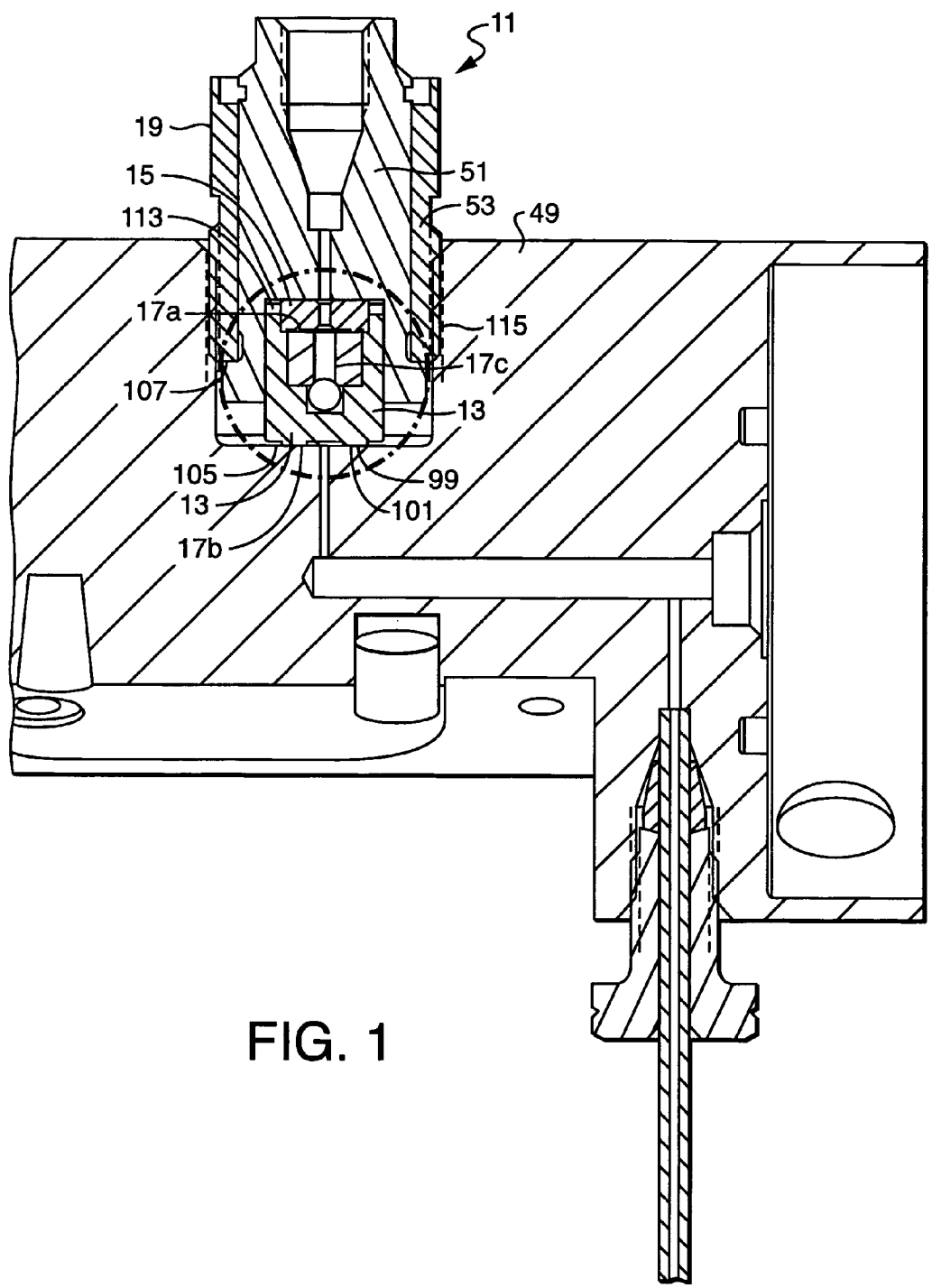
FIG. 1 depicts, in cross section, a side view of a device made in accordance with the present invention.

Turning now to FIG. 1, a device, for holding fluids at high pressures, generally designated by the numeral 11, is depicted. The device 11, for receiving and discharging fluids, is in the nature of a check valve. Device 11 comprises a first housing 13, an end cap 15, at least one seal coating 17 and compression means 19.

Figure 2:
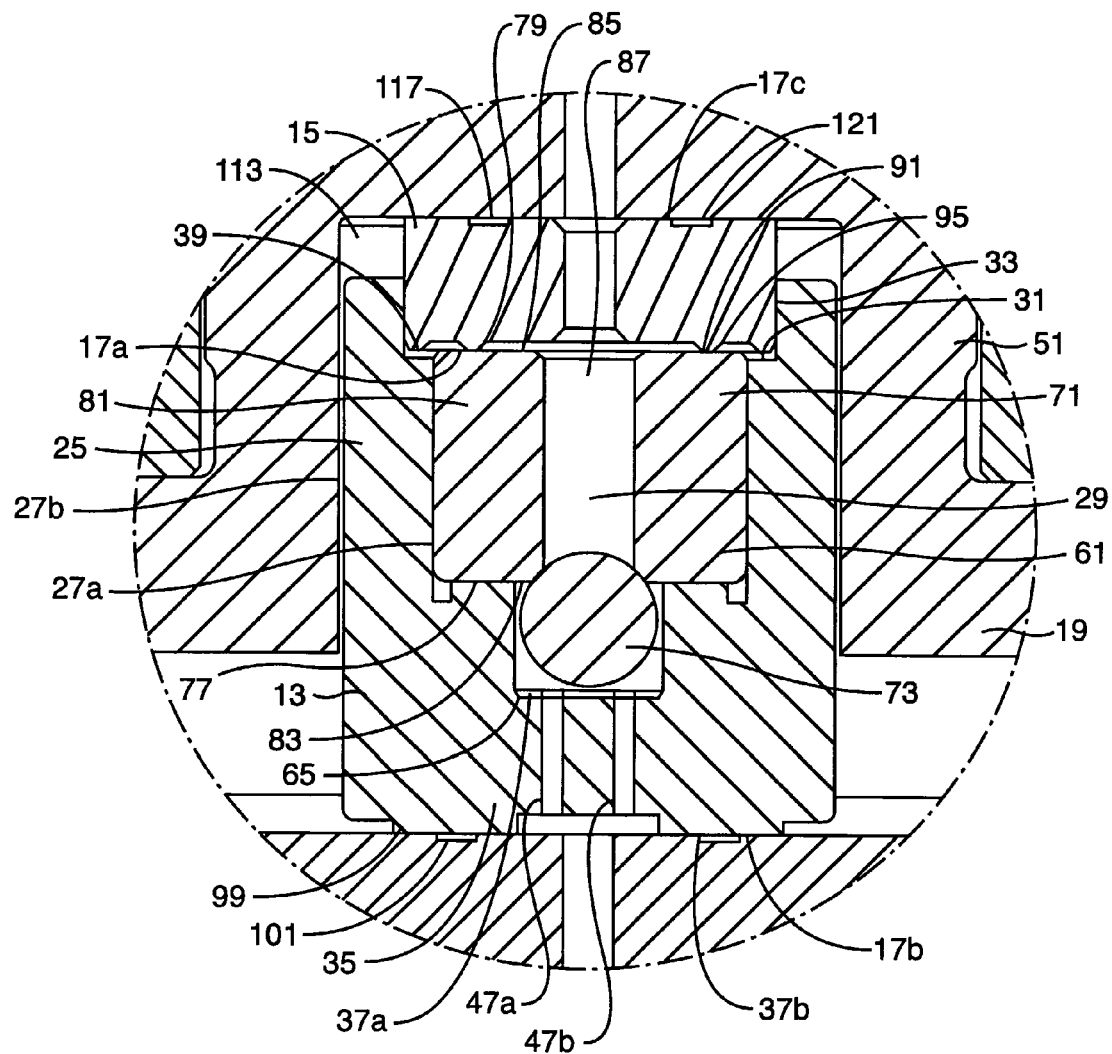
FIG. 2 depicts, in slight elevation, a view of an end cap of a device made in accordance with the present invention.

Turning now to FIG. 2, the first housing 13 has at least one side wall 25. Side wall 25 has an interior surface 27a and an exterior surface 27b. The interior surface 27a defines at least one chamber 29, preferably, cylindrical in shape. Interior surface 27a has at least one end cap abutment surface 31 for receiving the end cap 15. Preferably, the end cap abutment surface 31 is recessed into chamber 29 to facilitate positioning of the end cap 15. As depicted, interior surface 27 has a recess section 33 forming the recess for receiving end cap 15.

The housing 13 has an end wall 35 having an interior surface 37a and an exterior surface 37b. The end wall 35 closes the chamber 29 defined by the interior surface 27a of the side wall 25.

Figure 3:
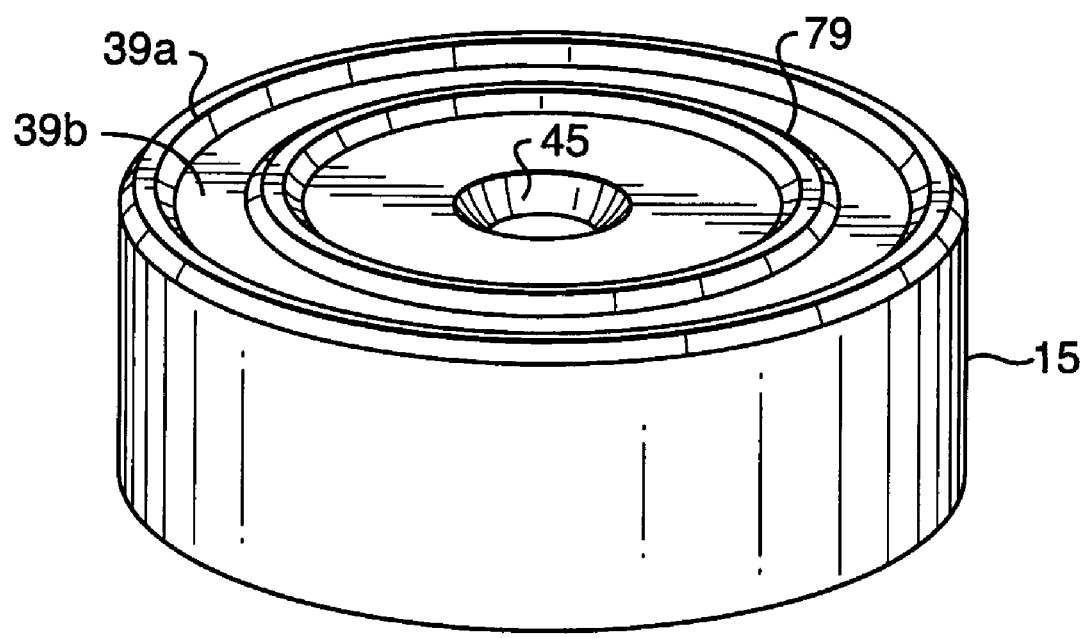
FIG. 3 depicts, in slight elevation a view of an end cap of a device made in accordance with the present invention.
Figure 4:
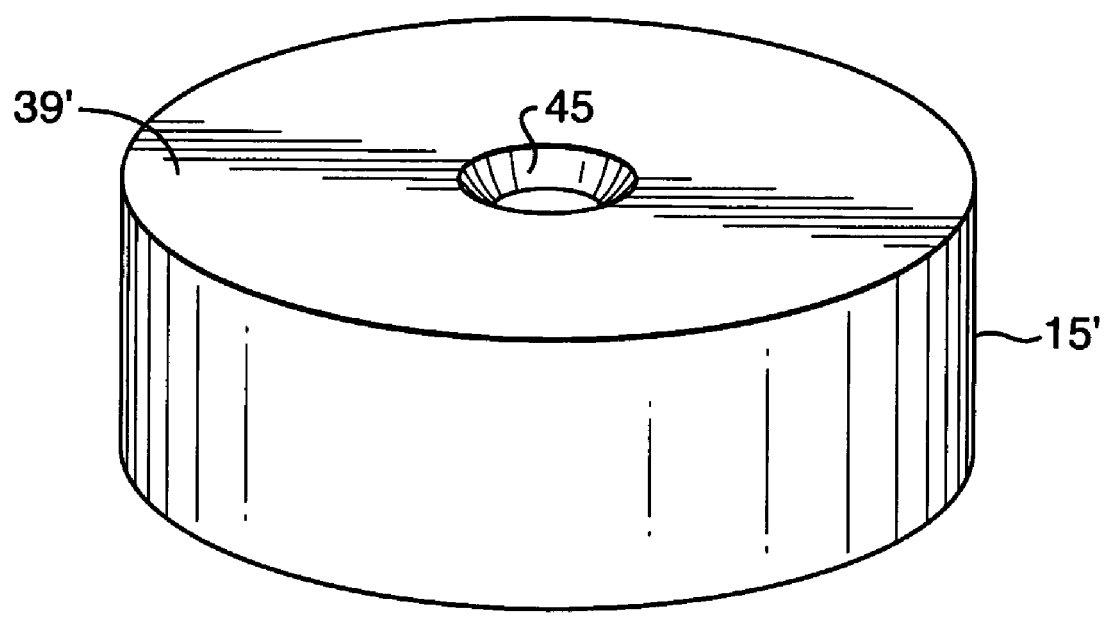
FIG. 4 depicts, in cross section, a side view of an end cap of a device made in accordance with the present invention.

End cap 15 is cylindrical in shape to cooperate with the recess section 33 of the interior surface 27a of the first housing 13. End cap 15 has at least one first housing abutment surface 39. Turning now to FIGS. 3 and 4, alternative embodiments of end cap 15 are disclosed. The end cap 15 of FIG. 2 is illustrated in greater detail in FIG. 3. End cap abutment surface 39 is a ridge 39a to localize compression forces on said seal coating 17. The ridge 39a is a protrusion jutting upward from a planar surface 39b. The ridge 39a is capable of contact with an opposing abutment surface such as end cap abutment surface 31 of the first housing 13. The ridge 39a localizes or focuses compression forces in a small area.

Turning now to FIG. 4, a further embodiment of the end cap 15 is illustrated, generally designated by the numeral 15'. End cap 15' is cylindrical in shape to cooperate with the recess section 33 of the interior surface 27a of the first housing 13. End cap 15' has at least one first housing abutment surface 39'. In this embodiment, the first housing abutment surface 39' is planar, without any protruding surface features. The abutment surface 39' is capable of contact with an opposing abutment surface such as end cap abutment surface 31 of first housing 13.

The first housing abutment surface 31 receives the end cap abutment surface 39 and 39" positioning the end cap 15 and/or 15' on the first housing 13 for enclosing the chamber 29. The end cap 15 and/or 15' and first housing are typically made of stainless steel; however, other materials can readily be substituted. In the case where, the first housing 13 and end cap 15 and/or 15' are parts of a check valve, the first housing 13 is approximately 0.25 to 0.75 mm in length and diameter. The end cap 15 and or 15' are approximately 0.1 to 0.70 in diameter and 0.1 to 0.2 mm in thickness.

At least one of the first housing abutment surface 39 and/or 39' and the end cap abutment surface 31 has first seal coating 17. The first seal coating 17 comprises a deformable plastic adhering to first housing abutment surface 31 and/or 31' or the end cap abutment surface 39. Seal coating 17 is selected from one or more of the polymeric coatings consisting of polytrifluoroethylene (PTFE), polyetheretherketone (PEEK), polychlorotrifluoroethylene (PCTFE), perfluoroalkoxy (PFA) and fluorinatedethylenepropylene (FEP). The polymeric coating is applied to the entire end cap 15 and/or 15' or the first housing abutment surface 31 and/or 31' to a thickness of 0.0005-0.0025 inches, and most preferably, approximately 0.0010 to 0.0015 inches. Methods of placing a polymeric coating on a metal substrate are well known in the art.

The device 11 further comprises fluid path means for receiving and removing fluid from the chamber. Referring now to FIGS. 3 and 4, the end cap 15 and 15' have an end cap opening 45. And, returning now to FIG. 1, the first housing has a first housing opening or more preferably a pair of first housing openings 47a and 47b for introducing fluids into the chamber 29. Preferably, the pair of openings are set off axis for check valve applications in end wall 35.

The end cap opening 45 and first housing openings 47a and 47b may comprise any ports, conduits and pipes that provide fluid. Thus, embodiments of the present invention can be placed inline, with fluid path means comprising conduits and pipes or incorporated within the housing of a larger structure, for example, without limitation, as depicted in FIG. 1, a pump head or pump housing 49.

The device 11 comprises compression means 19 to compress the end cap 15 and/or 15', with the end cap abutment surface 31 and/or 31' received on said first housing abutment surface 39, towards said first housing 13. The compression deforms the first seal coating 17 and seals the chamber. As illustrated in FIG. 1, the compression means 19 comprises pump housing 49, compression housing 51 and screw fitting 53.

It will be recognized by those skilled in the art that pump housing 49 may be substituted with a further fitting that cooperates with compression housing 51 and screw fitting 53, to allow the device 11 to be placed in a fluid line.

Embodiments of the present invention are ideally suited for fittings and valves. Where the device is in the form of a valve, referring to FIG. 2, the chamber 29 contains a valve assembly 61. The valve assembly 61 may comprise rotary-type valves (not shown), gated valves (not shown) or check valves, to described in further detail.

In the case where the device is in the form of a check valve, the first housing 13 has at least one end wall 65 opposite the end cap 15 or 15'. The fluid path means comprises at least one opening 45 in said end cap 15 or 15' and at least one opening, and preferably two, 47a and 47b, in said end wall 65. Chamber 29 holds a valve assembly 61 comprising a ball seat 71 and a ball 73.

Preferably, the interior wall 27a has a first ball seat abutment surface 77. And, the end cap 15 and/or 15' has a ball seat abutment surface 79. The ball seat 71 comprises a cylinder section 81 having a first rim 83, a second rim 85 and a fluid passage 87. The first rim 83 has a ball receiving surface 89 for engaging the ball 73 and closing the fluid passage 87. Second rim 85 has a rim abutment surface 91 and end cap 15 and/or 15' has a ball seat abutment surface 79. Preferably, at least one of the rim abutment surface 91 and ball seat abutment surface 79 has a ball seat seal coating 95. The ball seat seal coating 95 engages the abutment surface opposite to that it is placed and seals the ball seat and the housing 13 and/or end cap 15 and/or 15'. The ball seat coating 95 may comprise a portion of the seal coating 17 on the end cap 15 and/or 15'. Preferably, the ball seat coating is made and formed as described above with respect to the seal coating 17.

The exterior surface 37b of end wall 35 has an end wall abutment surface 99 encircling the one or more end wall openings 47a and 47b. Preferably, the end wall abutment surface 99 has an end wall seal coating 101. The end wall seal coating 101 is a deformable plastic made and formed as described above with respect to the seal coating 17. The end wall seal coating 101 sealably engages an adjoining wall to which it is compressed.

Devices of this type are well suited to be mounted in a further major housing structure having the adjoining wall. For example, turning now to FIG. 1, the end wall seal coating 101 engages the adjoining wall 105 of a pump head housing 49. In this embodiment, preferably, the adjoining wall 105 has an opening 103 for the passage of fluid into the end wall opening (not shown). In this embodiment, the compression means 19 comprises such adjoining wall 105 and a cylindrical wall 107 for receiving the end wall abutment surface 99 and compressing the end wall seal coating 101 in sealing engagement. The compression means 19 comprises a compression assembly comprising a compression housing 51 and compression sleeve 53. The compression housing 51 has a compression chamber 113 for receiving the first housing 13 and the end cap 15 and/or 15'. The compression sleeve 53 engages the compression housing 51 for placing said end cap 15 and/or 15', and first housing 13 under compression.

Preferably, the compression sleeve 53 and compression nut (not shown) or the pump head 49 or other apparatus to which it is placed has cooperating threads 115 as depicted in FIG. 1. The cooperating threads 115 engage upon relative rotation of the compression sleeve and pump housing 49 or compression nut (not shown).

Turning now to FIG. 2, the compression housing 51 has an second end cap abutment surface 117. At least one of the end cap 15 and/or 15' has a compression assembly seal coating 121. The compression assembly seal coating 121 is a deformable plastic made and formed as described above with respect to the seal coating 17. The compression assembly seal coating 121 sealably engages an adjoining wall to which it is compressed.

In operation, a method of using the present invention to joining fluid passages comprises the steps of providing a device 11 having a first housing 13, an end cap 15 and or 15', a seal coating 17 and compression means 19. The device has a fluid path means for receiving and removing fluid from the chamber 29. The method further comprises the step of placing the receiving conduit and discharge conduits in communication with the fluid passages and compressing the seal coating 17 to seal the chamber 29.

The devices and methods of the present invention are ideally suited for high pressure applications. The devices made in accordance of the present invention do not have seals that exhibit material creep, cold flow and relaxation. That is, as the fluid pressure fluctuates, the seal coating do not move. The seal coatings are adhered to or fixed to one of the abutment surfaces. As such the seal coasting can not move or slip from an original position. Thus, embodiments of the present invention provide devices which do not have gasket failure.

These and other advantages and features will be apparent to those skilled in the art to which this invention relates and therefore the present invention should not be limited to the precise details disclosed herein but should encompass the subject matter of the claims that follow.

The invention claimed is:

1. A fluid control device, comprising:
   a housing having a chamber therein defined by an interior surface comprising an end wall;
   a valve assembly disposed in the chamber to control fluid flow through the chamber, the valve assembly comprising a valve seat having an outer surface disposed adjacent to the interior surface of the chamber;
   an end cap disposed in the housing opposite the end wall to enclose the chamber, the end wall, the valve seat and the end cap each having an opening therein to pass a fluid to the chamber or to remove a fluid from the chamber, the housing and the end cap each having an abutment surface to receive the other abutment surface, at least one of the abutment surfaces having a plastic seal coating; and
   compression means to engage the end cap to deform the plastic seal coating between the abutment surfaces and thereby seal the chamber.

2. The fluid control device of claim 1, wherein the abutment surface of the housing is disposed near an end of the housing.

3. The fluid control device of claim 2 wherein the end of the housing is formed with a recess into which the end cap is received and wherein the abutment surface of the housing comprises an annular surface within the recess.

4. The fluid control device of claim 3 wherein the abutment surface of the end cap cooperates with the annular surface and includes an annular ridge that localizes compression forces on the plastic seal coating.

5. The fluid control device of claim 1 wherein the valve assembly comprises a ball check valve and wherein the valve seat is a ball seat, the ball check valve having a ball disposed in the chamber between the end cap and the end wall of the chamber, the ball seat having an opening to provide fluid communication between the openings in the end wall and the end cap, the ball seat having a ball receiving surface for engaging the ball to control the flow of fluid through the chamber and having an abutment surface cooperating with the abutment surface of the end cap.

6. The fluid control device of claim 5 wherein the abutment surface of the end cap which cooperates with the abutment surface of the ball seat comprises an annular ridge.

7. The fluid control device of claim 5 wherein the opening in the end wall to pass a fluid extends through the housing.

8. The fluid control device of claim 1 wherein the end cap is disposed at a first end of the housing and wherein the housing has a second end opposite the first end, the second end of the housing configured to cooperate with an adjoining wall of an apparatus in which the fluid control device is disposed, at least one of the second end of the housing and the adjoining wall having a plastic seal coating.

9. The fluid control device of claim 1 wherein the end cap has an additional abutment surface remote to the abutment surface that receives the housing abutment surface, the additional abutment surface configured to cooperate with a surface of the compression means, at least one of the additional abutment surface and the surface of the compression means having a plastics seal coating.

10. The fluid control device of claim 1 wherein the compression means comprises a compression housing having a compression chamber in which the housing and the end cap are received, the compression means further comprising a compression sleeve that cooperates with the compression housing to cause a compression between the housing and the end cap.

11. The fluid control device of claim 1 wherein the plastic seal coating comprises a polymeric coating comprising one of polytrifluoroethylene (PTFE), polyetheretherketone (PEEK), polychlorotrifluoroethylene (PCTFE), perfluoroalkoxy (PFA) and fluorinatedethylenepropylene (FEP).

* * * * *